United States Patent
Zhang

(10) Patent No.: US 9,217,730 B2
(45) Date of Patent: Dec. 22, 2015

(54) INPUT-PROTECTED STRUCTURAL HEALTH MONITORING SYSTEM

(75) Inventor: Chang Zhang, San Jose, CA (US)

(73) Assignee: ACELLENT TECHNOLOGIES, INC., Sunnyvale, CA (US)

( * ) Notice: Subject to any disclaimer, the term of this patent is extended or adjusted under 35 U.S.C. 154(b) by 956 days.

(21) Appl. No.: 12/781,639

(22) Filed: May 17, 2010

(65) Prior Publication Data

US 2011/0279233 A1    Nov. 17, 2011

(51) Int. Cl.
*G01B 3/44* (2006.01)
*G01N 29/24* (2006.01)
*G01M 5/00* (2006.01)
*G01N 29/42* (2006.01)

(52) U.S. Cl.
CPC ........... *G01N 29/245* (2013.01); *G01M 5/0033* (2013.01); *G01N 29/42* (2013.01); *G01N 2291/0258* (2013.01)

(58) Field of Classification Search
CPC ............ G01M 5/0066; G01M 5/0041; G01M 5/0033; G01M 5/0083; G01M 5/0091; G01N 2291/106; G01N 29/07
USPC .................. 702/34, 81, 94, 104, 144; 73/594
See application file for complete search history.

(56) References Cited

U.S. PATENT DOCUMENTS

| | | | |
|---|---|---|---|
| 7,387,033 B2 * | 6/2008 | Qing et al. | 73/862.046 |
| 2006/0042396 A1 * | 3/2006 | Qing et al. | 73/786 |
| 2006/0079747 A1 * | 4/2006 | Beard et al. | 600/407 |
| 2006/0283266 A1 * | 12/2006 | Qing et al. | 73/862.041 |
| 2007/0012112 A1 * | 1/2007 | Kim | 73/594 |
| 2008/0253231 A1 * | 10/2008 | Yu et al. | 367/140 |
| 2009/0157358 A1 * | 6/2009 | Kim | 702/185 |
| 2010/0161283 A1 * | 6/2010 | Qing et al. | 702/188 |
| 2012/0065901 A1 * | 3/2012 | Bechhoefer et al. | 702/34 |

OTHER PUBLICATIONS

David C. Zhang, Pin Yu, Shawn Beard, Peter Qing, Amrita Kumar and Fu-Kuo Chang; A New SMART Sensing System for Aerospace Structures; Apr. 27, 2007; Acellent Technologies, Inc., 835 Stewart Drive, Sunnyvale, CA, USA 94085 Department of Aeronautics and Astronautics, Stanford University, Stanford, CA, USA 94305; Proc. of SPIE vol. 6561 656107 pp. 1-10.*

* cited by examiner

*Primary Examiner* — Eliseo Ramos Feliciano
*Assistant Examiner* — Eman Alkafawi
(74) *Attorney, Agent, or Firm* — Innovation Counsel LLP

(57) ABSTRACT

A structural health monitoring (SHM) system that protects its active and passive components with filter circuits, instead of switches. The active module of the SHM system utilizes a high pass filter, and the passive module of the SHM system utilizes a low pass filter. The active module transmits its interrogating, or excitation, signals at relatively high frequencies that are filtered out by the low pass filter of the passive module, preventing the passive module from sustaining any damage due to the high voltage excitation signals. Meanwhile, the high frequency interrogating signals are passed to the active module's circuitry by its high pass filter, where they can be analyzed accordingly.

19 Claims, 2 Drawing Sheets

INPUT-PROTECTED STRUCTURAL HEALTH MONITORING SYSTEM

GOVERNMENT RIGHTS

The U.S. Government has a paid-up license in this invention and the right in limited circumstances to require the patent owner to license others on reasonable terms as provided for by the terms of Contract No. FA9550-08-C-0048 awarded by the Air Force Office of Scientific Research.

BRIEF DESCRIPTION

This invention relates generally to structural health monitoring. More specifically, this invention relates to input-protected structural health monitoring systems.

BACKGROUND

The structural health monitoring (SHM) field often aims at carrying out the diagnostics and monitoring of structures using sensor (commonly, transducer) arrays connected to associated hardware, such as dedicated analyzers. When connected to a computer, this hardware can allow users to determine the integrity of structures, often in, or close to, real time. In this manner, SHM systems and techniques can go beyond simple detection of structural failure, to providing additional useful information such as early indications of damage.

However, SHM systems still suffer from drawbacks. For example, it is often desirable to configure SHM systems with both "active" and "passive" components. The active components transmit excitation signals to the transducers, generating diagnostic stress waves in the structure being monitored. These waves are picked up by neighboring sensors, and the resulting signals are analyzed to determine the health of the structure. In some approaches, differences between the signals sent to the transducers and those received back from other sensors, or differences between received signals and a stored set of baseline data, can indicate damage to the structure.

In contrast, the passive components are not used to generate such interrogating waveforms. Rather, they passively monitor the structure, "listening" to detect stress waves generated in the structure by some event (e.g., an impact, or operation of the structure). When stress waves exceeding a specified threshold are detected, the system records/analyzes them to determine information such as whether an impact occurred, its location, and force.

It is often desirable to utilize both passive and active components in a single SHM system. In such cases, it is further desirable to use the same transducers (i.e., sensors/actuators) for both active sensing and passive sensing. This typically entails connecting both the passive and active components to the same transducers, which also means that both the passive and active components are electrically connected to each other. However, such configurations currently face significant challenges. For example, excitation signals from active components are often high voltage signals, and must be blocked from the passive system so as to avoid damaging the sensitive circuitry of the passive system with excessively large voltage pulses.

Such blocking is often accomplished via high-voltage switches placed between the transducers and passive system circuitry, with the switches being opened during operation of the active system so that the passive system is disconnected from the active system during operation of the active system. However, as a separate switch is often desired for each transducer, large transducer arrays can often require big, bulky banks of switches that can be complicated and expensive to implement. Additionally, the switches are often operated via custom software that must be written, adding to time and expense.

SUMMARY

The invention can be implemented in a number of ways, such as by a structural health monitoring system.

In one embodiment, a structural health monitoring system comprises an active damage detection module operable to transmit interrogation signals for interrogating a structure, the active damage detection module comprising a signal transmitter operable to transmit ones of the interrogation signals having a first frequency. The system also includes a passive monitoring module operable to monitor the structure, the passive monitoring module in electrical communication with the signal transmitter of the active damage detection module. The passive monitoring module comprises a signal filter operable to receive the interrogation signals from the signal transmitter, to attenuate the received interrogation signals at the first frequency, and to substantially pass received signals at a second frequency that is different from the first frequency.

In another embodiment, a structural health monitoring system comprises an active damage detection module operable to transmit interrogation signals for interrogating a structure, and a passive monitoring module operable to monitor the structure. The passive monitoring module has an analyzer in electrical communication with the active damage detection module when the active damage detection module transmits the interrogation signals, so that the analyzer receives the transmitted interrogation signals.

Other aspects and advantages of the invention will become apparent from the following detailed description taken in conjunction with the accompanying drawings which illustrate, by way of example, the principles of the invention.

BRIEF DESCRIPTION OF THE DRAWINGS

For a better understanding of the invention, reference should be made to the following detailed description taken in conjunction with the accompanying drawings, in which.

Like reference numerals refer to corresponding parts throughout the drawings.

DETAILED DESCRIPTION OF EMBODIMENTS OF THE INVENTION

In one embodiment, the invention relates to an SHM system that protects its active and passive components with filter circuits instead of switches. The active module of the SHM system utilizes a high pass filter, and the passive module of the SHM system utilizes a low pass filter. The active module transmits its interrogating, or excitation, signals at relatively high frequencies that are filtered out by the low pass filter of the passive module, preventing the passive module from sustaining any damage due to the high voltage excitation signals. Meanwhile, the high frequency interrogating signals are passed to the active module's circuitry by its high pass filter, where they can be analyzed accordingly. When compared to the switches described above, these high- and low-pass filters can provide for an SHM system whose passive module is input-protected from its active system in a much cheaper, more compact, and easy-to-implement manner.

Figure 1:
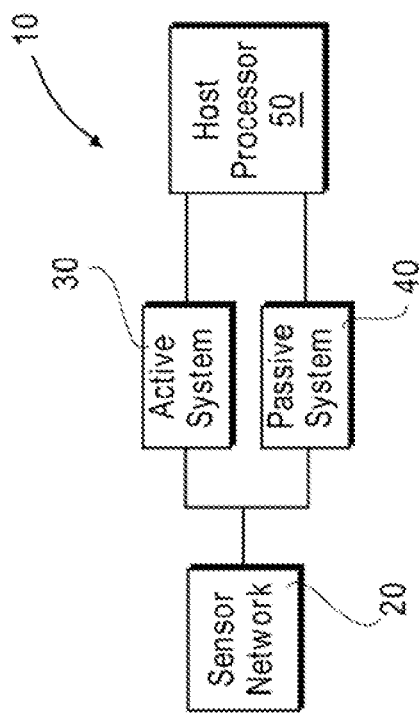
FIG. 1 is a block diagram illustration of an SHM system incorporating passive and active components, according to embodiments of the invention.

FIG. 1 is a block diagram illustration of an SHM system incorporating both high- and low-pass filters, in accordance with one exemplary embodiment of the invention. Here, SHM system 10 includes a sensor network 20, active system 30, passive system 40, and host processor 50. The sensor network 20 is made up of a number of sensing elements that are affixed to a structure in a manner that allows them to transmit and detect stress waves in the structure.

The active system 30 transmits high voltage electrical waveforms to selected sensing elements of the sensor network 20, causing them to transmit stress waves in the structure. These stress waves are received at other sensing elements, which generate corresponding electrical signals and transmit them to the active system 30 for conditioning and analysis. As the electrical waveforms transmitted by the active system 30 are known, comparison of the signals generated by the sensing elements to these known waveforms, or comparison of the signals from the sensing elements to stored baseline signals can indicate whether damage has occurred, or whether the structure has changed in some other way.

The passive system 40 does not transmit electrical waveforms to the sensing elements of sensor network 20. Rather, it listens to the sensing elements, detecting and analyzing electrical signals generated by the sensing elements. The passive system 40 is useful for detecting other stress waves besides those generated by the active system 30, where these other stress waves can be of much smaller amplitudes than those generated by the active system 30. The passive system 30 is thus useful for detecting the occurrence of events such as impacts, but must also often be more sensitive than the active system 30.

It is noted that, despite this increased sensitivity, the passive system 40 is connected directly to the active system 30, and both systems 30, 40 are each directly connected to the same sensing elements of sensor network 20. That is, the active system 30, passive system 40, and sensing elements of sensor network 20 are all in electrical communication with each other via common wires, as shown. In many conventional SHM systems, such a configuration would result in high voltage signals from the active system 30 damaging or destroying the sensitive circuitry of the passive system 40. Alternatively, as above, conventional SHM systems isolate their passive systems from their active systems with banks of switches that can be expensive, bulky, and laborious to implement.

Embodiments of the invention overcome this problem by employing a high-pass filter in the active system 30, a low-pass filter in the passive system 40, and transmitting the high-voltage electrical waveforms from the active system 30 at frequencies that are sufficiently high to be attenuated by the low-pass filter. In this manner, the active system 30 queries the structure at frequencies that are filtered out by the passive system 40, allowing for both active system 30 and passive system 40 to operate while remaining connected to the same sensor network 20. Furthermore, the need for switches is eliminated, thus reducing the overall cost and complexity of SHM system 10.

The active system 30 and passive system 40 can be controlled by a controller such as host processor 50. In operation, the host processor 50 directs the active system 30 to query the structure (i.e., to transmit stress waves through the structure, effectively interrogating or querying it), to detect the resulting stress waves, and process/analyze the resulting electrical signals. The host processor 50 also analyzes those signals detected by the passive system 40. Embodiments of the invention contemplate location of the host processor 50 anywhere, including within one or more of the active system 30 or passive system 40, as well as remote. Embodiments also contemplate any division of tasks between the host processor 50 on one hand, and the active system 30 and passive system 40 on the other. For example, the invention includes embodiments in which the host processor 50 simply directs the active system 30 to scan the structure in a particular manner, and the active system 30 performs any ensuing tasks, such as determining which interrogating waveform(s) to employ, selecting which sensing elements to transmit the waveform(s) to, and which sensing elements will be used to detect the resulting stress waves. Conversely, the invention also includes embodiments in which the host processor 50 executes each of these tasks, and the active system 30 simply carries out the corresponding directives from the host processor 50.

The system 10 can be constructed with the host processor 50 as part of a host device such as a desktop or portable computer, where the active system 30 and passive system 40 are parts of a plug-in peripheral or card. The system 10 can also be constructed with all three of these components integrated into a single device. Embodiments of the invention contemplate any arrangement of active system 30 and passive system 40.

The sensing elements of sensor network 20 can be any set of sensors and/or actuators capable of detecting and transmitting stress waves, respectively. Typically, a sensor network 20 includes multiple actuating and/or sensing elements placed at discrete locations on the structure, for transmitting stress waves through a structure and detecting resulting waveforms, respectively. As is known, sensors can both passively monitor a structure for stress waves resulting from an impact (whereupon analysis of such stress waveforms can be performed to determine data about any corresponding damage), and monitor the structure for stress waves actively transmitted through the structure by the actuators (whereupon comparison of the resulting waveforms to the original signals transmitted can indicate damage). The invention contemplates use of any sensors and any actuators, affixed to a structure in any manner and any number that allow for evaluation of the structure. However, one suitable sensor/actuator is lead zirconate titanate (PZT) piezoelectric transducers (or any other suitable transducer) that each can act as both a sensor and an actuator. In known manner, each PZT transducer converts electrical signals to stress waves in order to actively query a structure, and converts resulting detected stress waves to electrical signals for analysis.

Furthermore, the sensors/actuators can be individually affixed to a structure, or affixed to a flexible diagnostic layer that can itself be affixed to a structure. This diagnostic layer and its operation are further described in U.S. Pat. No. 6,370,964 to Chang et al., which is hereby incorporated by reference in its entirety and for all purposes. Construction of the diagnostic layer is also explained in U.S. Pat. No. 7,413,919 to Qing et al., which is also incorporated by reference in its entirety and for all purposes.

Figure 2:
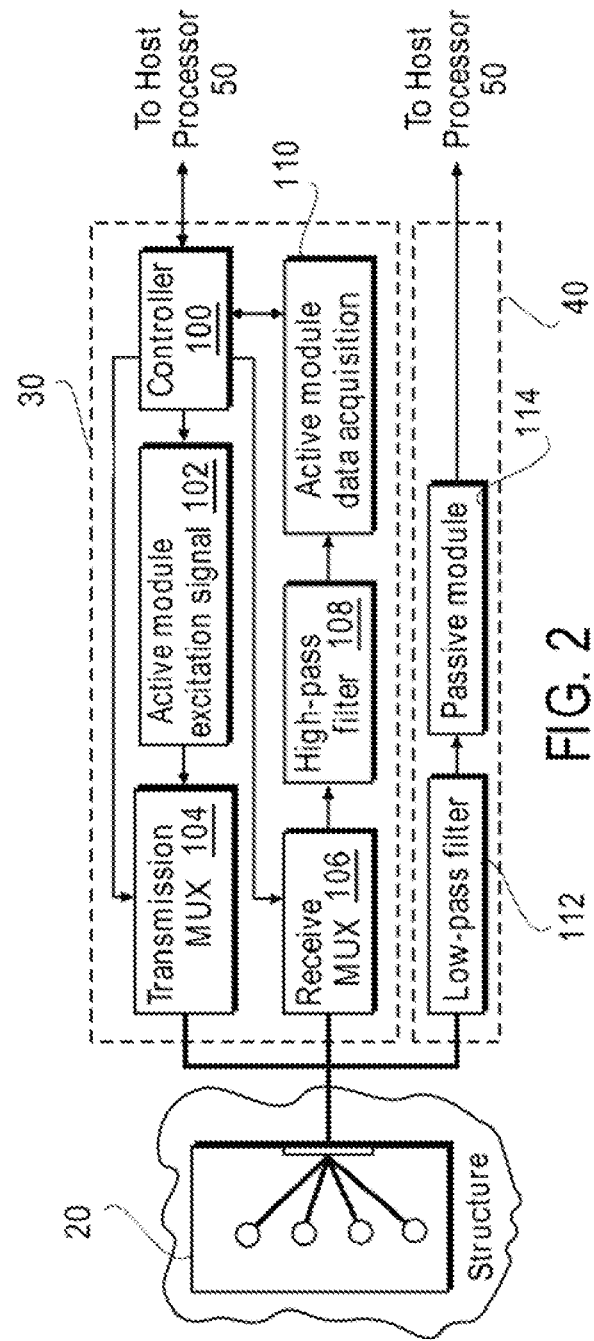
FIG. 2 illustrates further details of the active and passive systems of FIG. 1.

FIG. 2 illustrates further details of the active and passive systems of FIG. 1. Here, the active system 30 contains a controller 100, excitation signal module 102, transmission multiplexer (MUX) 104, receive MUX 106, high pass filter 108, and data acquisition module 110. The excitation signal module 102 stores waveforms for use in generating interrogating signals, and generates interrogating signals having those waveforms when instructed by the controller 100. The transmit MUX 104 is a multiplexer that directs interrogating signals to specified transducers of sensor network 20. Similarly, the receive MUX 106 is a multiplexer that receives signals back from the sensor network 20, and transmits signals from specified transducers to the high-pass filter 108. The controller 100 communicates with each of the excitation signal module 102, transmission MUX 104, receive MUX 106, and data acquisition module 110.

The active system 30 and passive system 40 are each electrically connected to the same sensor network 20, and are each therefore also electrically connected to each other. Signals sent from the active system 30 to the sensor network 20 are thus also sent to the passive system 40. Conversely, signals generated by the sensing elements of network 20 are sent to both the active system 30 and passive system 40.

In the active system 30, the interrogating signals are sent at a high frequency, so that the high-pass filter passes the corresponding signals detected by the transducers, and attenuates/filters out other signals. The data acquisition module 110 stores the signals from the high pass filter 108, and can either analyze the signals to determine structural health, or pass them on to the controller 100 and/or host processor 50 for analysis.

The passive system 40 contains a low pass filter 112 and data acquisition module 114. As the interrogating signals are high frequency signals, the low pass filter 112 attenuates any such signals it receives, substantially preventing them from reaching the sensitive circuitry of data acquisition module 114. However, the low pass filter 112 passes lower-frequency signals received by the transducers of sensor network 20. In this manner, signals transmitted by the active system 30 are attenuated by the low pass filter 112, while other, lower frequency signals are passed to the data acquisition module 114 of the passive system 40. The data acquisition module 114 stores and/or analyzes these lower frequency signals, passing on these signals and/or its analysis results to the host processor 50.

In operation, the sensor network 20 is attached to a structure as shown. The active module 30 can both transmit signals to, and receive signals from, the sensor network 20. The passive module 40 can receive signals from the sensor network 20, but does not transmit any signals thereto. The active module 30 and passive module 40 can operate essentially independent of each other, with the active module 30 actively scanning the structure and the passive module 40 monitoring the structure separately. When the active module 30 operates to scan the structure, the controller 100 directs the transmission MUX 104 to close (i.e., switch on) electrical connections for certain sensing elements of sensor network 20, thus identifying which transducers are to transmit the interrogating signals. The controller 100 also directs the receive MUX 106 to close electrical connections for specified other sensing elements of network 20, thus identifying which transducers are to detect the interrogating signals. The controller 100 then directs the excitation signal module 102 to generate interrogating electrical waveforms, which are sent through the transmission MUX 104 to those sensing elements for which MUX 104 has closed their electrical connections. Those selected transducers which receive these electrical waveforms then generate corresponding stress waves having the same or similar waveforms. These stress waves propagate through the structure, arriving at other sensing elements and causing them to generate electrical signals in response. These "received signals," which have waveforms corresponding to the stress waves received by the sensing elements, are transmitted to the receive MUX 106. If the received signals are transmitted by one of the sensing elements specified by the receive MUX 106 (i.e., ones for which the receive MUX 106 has a closed electrical connection), they are then transmitted to the high pass filter 108. As the interrogating electrical waveforms, and thus the received signals, are high frequency waveforms, the high pass filter 108 passes the received signals to the data acquisition module 110. The data acquisition module 110 can store, condition, and/or analyze the received signals, as well as pass the signals and/or analysis results to the controller 100 or host processor 50.

The received signals generated by the transducers of sensor network 20 are also received at the low pass filter 112. However, as above, the received signals have frequencies corresponding to the interrogating waveforms, which are selected to be of high frequency. The low pass filter 112 thus filters out, or substantially attenuates, these received signals instead of passing them to the data acquisition module 114. However, the low pass filter 112 passes lower-frequency signals generated by the sensing elements, so that the data acquisition module 114 analyzes lower-frequency stress waves which are not in the same frequency range as the interrogating stress waves generated by the active module 30.

Figure 3:
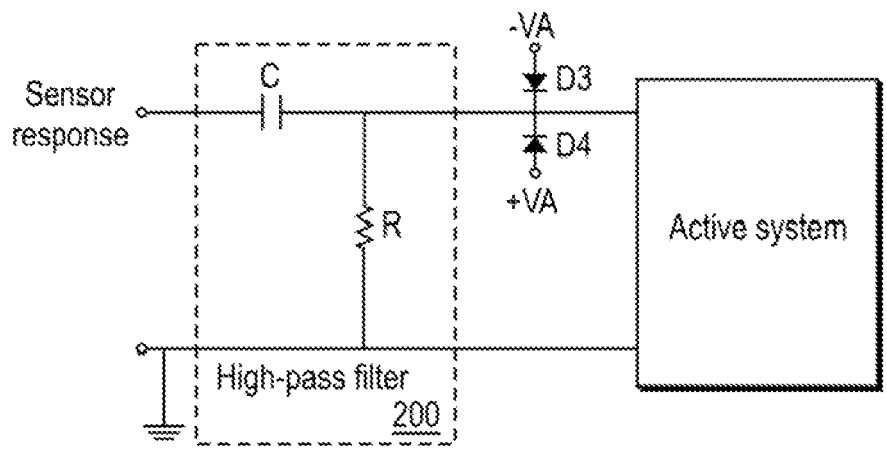
FIG. 3 illustrates a high pass filter for the active system of FIG. 1.
Figure 4:
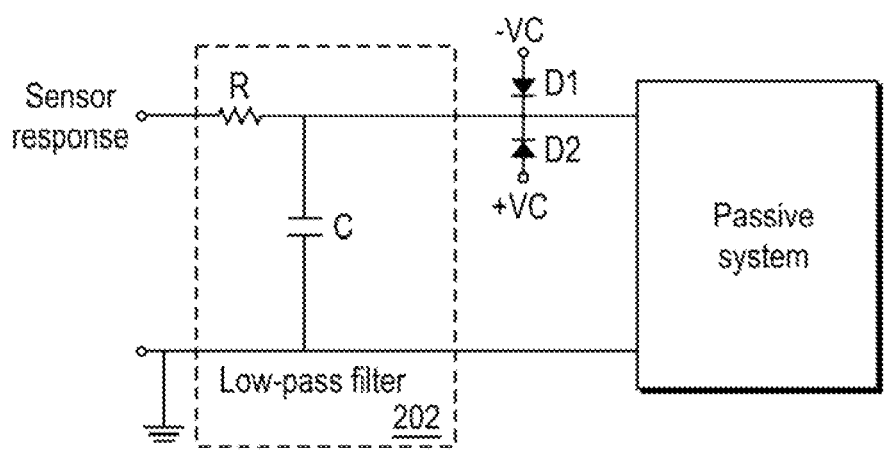
FIG. 4 illustrates a low pass filter for the passive system of FIG. 1.

The invention contemplates any suitable filter configurations for the high pass filter 108 and low pass filter 112. Exemplary filter configurations are shown in FIGS. 3-4. In FIG. 3, high pass filter 108 can include a number of filter circuits 200 each filtering the connection between one sensing element and the data acquisition module 110. That is, each of the connections shown in FIG. 2 running from the sensor network 20 to the receive MUX 106, to the high pass filter 108, and on to the data acquisition module 110, is actually a number of wires, with one pair of wires for each sensing element of sensor network 20. The high pass filter 108 thus contains a number of filter circuits 200, one connected to each wire pair, so that a filter circuit 200 filters signals from each sensing element.

FIG. 3 illustrates an embodiment in which each filter circuit 200 is connected to a wire pair from one sensing element. One wire from each pair is grounded as shown, while a capacitor is connected in series along the other wire, and a resistor is connected in parallel between the two wires. As can be observed, this configuration provides for a high pass filter circuit which passes high frequency signals on to the remaining components of the active system 30, such as data acquisition module 110. While the invention contemplates any suitable configuration for high pass filter circuit 200, one exemplary embodiment employs interrogating signals with frequencies in the range of approximately 10 kHz or greater, and corresponding R and C values of 1 kohm and 16 nF, respectively. Such a configuration effectively passes these 10 kHz+interrogating signals (and the signals received as a result of the corresponding stress waves generated in the structure), while attenuating lower frequencies. A higher order high pass filter can be used if desired, to provide a higher attenuation of low-frequency signals.

Diodes D3 and D4 provide further protection, by clamping signals transmitted to the active module 30 within the range [−VA−0.7, VA+0.7].

FIG. 4 illustrates further details of low pass filter 112. Like high pass filter 108, low pass filter 112 can include a number of filter circuits 202 each filtering a wire running between one sensing element and the data acquisition module 114. In the embodiment of FIG. 4, one wire from each wire pair is grounded, while a resistor is connected in series along the other wire, and a capacitor is connected in parallel between the two wires. This provides a low pass filter circuit that attenuates high frequency signals from the active module 30. While the invention contemplates any suitable configuration for low pass filter circuit 202, one exemplary embodiment employs interrogating signals with frequencies in the range listed above (10 kHz+), and corresponding R and C values of 1 kohm and 16 nF, respectively. Such a configuration provides a low pass filter with a cut-off frequency of approximately 10 kHz. In such an embodiment, the active system 30 can transmit interrogating waveforms at frequencies of approximately 50-1000 kHz, with the low pass filter 112 providing approximately 16-40 dB of attenuation for those frequencies, effectively preventing them from reaching and potentially damaging data acquisition module 114. Diodes D1 and D2 provide further protection, by clamping signals transmitted to the active module 30 within the range [−VC−0.7, VC+0.7].

It should be noted that embodiments of the invention contemplate any filter for passive module 40, so long as the filter is tuned to substantially attenuate the frequencies of the interrogating waveforms emitted from active system 30. More specifically, filter 112 can be a low pass filter or band pass filter, and can be configured to pass any suitable range of signal frequencies, so long as frequencies in the range of those from active system 30 are substantially attenuated.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. Many modifications and variations are possible in view of the above teachings. For example, embodiments of the invention include any configuration of active system 30 and passive system 40 in which the active system 30 transmits its interrogating waveforms at frequencies substantially filtered out by the passive system 40. That is, the passive system 40 can be equipped with any filter configured to filter frequencies generated by the active system 30. Furthermore, any circuit configurations for the high pass filter 108 and low pass filter 112 are contemplated. As another example, the sensors/actuators can be located on a flexible substrate or individually placed, and they (along with their substrate, if one is employed) can be affixed to an outer surface of a structure or embedded within. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A structural health monitoring system, comprising:
an active damage detection module operable to transmit interrogation signals for interrogating a structure, the active damage detection module comprising a signal transmitter operable to transmit one or more of the interrogation signals at a first frequency to a sensor network disposed on the structure; and
a passive monitoring module operable to monitor the structure, the passive monitoring module in electrical communication with the signal transmitter of the active damage detection module, the passive monitoring module comprising a first signal filter operable to receive the interrogation signals from the signal transmitter and response signals generated by the sensor network, to attenuate the received interrogation signals and the response signals at approximately the first frequency, and to pass un-attenuated response signals at approximately a second frequency that is different from the first frequency to a passive data acquisition module connected to the first signal filter;
wherein the active damage detection module further comprises:
a second signal filter operable to receive the interrogation signals from the signal transmitter and the response signals generated by the sensor network, to attenuate the response signals at approximately the second frequency, and to pass the received interrogation signals and un-attenuated response signals at approximately the first frequency to an active data acquisition module connected to the second signal filter.

2. The system of claim 1, wherein the first frequency is higher than the second frequency, and wherein the first signal filter is a low pass filter configured to attenuate the received interrogation signals and the response signals at approximately the first frequency and to pass the un-attenuated response signals at approximately the second frequency.

3. The system of claim 2, wherein the first frequency is greater than approximately 10 kHz, and wherein the second frequency is less than approximately 10 kHz.

4. The system of claim 2, wherein the first signal filter has a cut-off frequency that is approximately 10 kHz.

5. The system of claim 1, wherein the
active data acquisition module is operable to determine a health of the structure according to the passed signals from the second signal filter.

6. The system of claim 5, wherein the first frequency is higher than the second frequency, and wherein the second signal filter is a high pass filter configured to attenuate the response signals at approximately the second frequency and to pass the received interrogation signals and the un-attenuated response signals at approximately the first frequency to the active data acquisition module.

7. The system of claim 6, wherein the first frequency is greater than approximately 10 kHz, and wherein the second frequency is less than approximately 10 kHz.

8. The system of claim 6, wherein the first signal filter has a cut-off frequency that is approximately 10 kHz.

9. A structural health monitoring system, comprising:
an active damage detection module comprising a signal transmitter operable to transmit interrogation signals to a sensor network on a structure, so as to interrogate the structure; and
a passive monitoring module operable to monitor the structure, and comprising a first signal filter and an analyzer in electrical communication with the active damage detection module, wherein the first signal filter is operable to receive the interrogation signals from the active damage detection module and response signals generated by the sensor network, to attenuate the received interrogation signals and the response signals at approximately a first frequency, and to pass un-attenuated response signals at approximately a second frequency to the analyzer connected to the first signal filter;
wherein the active damage detection module further comprises:
a second signal filter operable to receive the interrogation signals from the signal transmitter and the response signals generated by the sensor network, to attenuate the response signals at approximately the second frequency, and to pass the received interrogation signals and un-attenuated response signals at approximately the first frequency to an active data acquisition module connected to the second signal filter.

10. The system of claim 9:
wherein the received interrogation signals and a portion of the response signals have higher frequencies than the second frequency; and
wherein the first signal filter is a low pass filter operable to attenuate the received interrogation signals and the portion of the response signals at approximately the higher frequencies, and to pass the un-attenuated response signals at approximately the lower second frequency to the analyzer for analysis.

11. The system of claim 10, wherein the received interrogation signals and the portion of the response signals have a frequency greater than approximately 10 kHz, and the second frequency is less than approximately 10 kHz.

12. The system of claim 10, wherein the first signal filter has a cut-off frequency that is approximately 10 kHz.

13. The system of claim 9, wherein the
active data acquisition module is operable to determine a health of the structure according to the passed signals from the second signal filter.

14. The system of claim 13, wherein the first frequency is higher than the second frequency, and wherein the second signal filter is a high pass filter configured to attenuate the response signals at approximately the second frequency and to pass the received interrogation and the un-attenuated response signals at approximately the first frequency to the active data acquisition module.

15. The system of claim 14, wherein the first frequency is greater than approximately 10 kHz, and wherein the second frequency is less than approximately 10 kHz.

16. The system of claim 14, wherein the first signal filter has a cut-off frequency that is approximately 10 kHz.

17. A method of driving a structural health monitoring system, comprising:
transmitting interrogation signals to a sensor network on a structure so as to interrogate the structure;
receiving the interrogation signals and response signals generated by the sensor network;
attenuating the received interrogation signals and the response signals at approximately a first frequency using a first signal filter, and
passing un-attenuated response signals at approximately a second frequency from the first signal filter to an analyzer; and
attenuating the response signals at approximately the second frequency using a second signal filter, and
passing the received interrogation and the un-attenuated response signals at approximately the first frequency from the second signal filter to an active data acquisition module.

18. The method of claim 17, wherein the received interrogation signals and a portion of the response signals have higher frequencies than the second frequency, the method further comprising:
attenuating the received interrogation signals and the portion of the response signals at approximately the higher frequencies, and
passing the un-attenuated response signals at approximately the second frequency to the analyzer.

19. The method of claim 17, wherein the first frequency is higher than the second frequency.

* * * * *